(12) United States Patent
Ohishi

(10) Patent No.: US 6,845,142 B2
(45) Date of Patent: Jan. 18, 2005

(54) IMAGE PROCESSING INVOLVING CORRECTION OF BEAM HARDENING

(75) Inventor: Satoru Ohishi, Otawara (JP)

(73) Assignee: Kabushiki Kaisha Toshiba, Tokyo (JP)

(*) Notice: Subject to any disclaimer, the term of this patent is extended or adjusted under 35 U.S.C. 154(b) by 78 days.

(21) Appl. No.: 10/175,780

(22) Filed: Jun. 21, 2002

(65) Prior Publication Data

US 2003/0031299 A1 Feb. 13, 2003

(30) Foreign Application Priority Data

Jun. 21, 2001 (JP) .......................................... 2001-188237

(51) Int. Cl.⁷ .............................................. A61B 6/03
(52) U.S. Cl. .................................. 378/8; 378/4; 378/901
(58) Field of Search .................... 378/4, 8, 15, 19, 378/901

(56) References Cited

U.S. PATENT DOCUMENTS

| | | | |
|---|---|---|---|
| 5,029,586 A | | 7/1991 | Honda |
| 5,528,644 A | | 6/1996 | Ogawa et al. |
| 5,953,444 A | * | 9/1999 | Joseph et al. ............... 382/131 |
| 6,600,801 B2 | * | 7/2003 | Raupach ........................ 378/4 |
| 2003/0053597 A1 | * | 3/2003 | Flohr et al. ................. 378/156 |

FOREIGN PATENT DOCUMENTS

| | | |
|---|---|---|
| JP | 6-142094 | 5/1994 |
| JP | 7-204197 | 8/1995 |

OTHER PUBLICATIONS

P. M. Joseph, et al., Medical Physics, vol. 24, No. 10, XP–001031919, pp. 1629–1634, "A Method for Simultaneous Correction of Spectrum Hardening Artifacts In CT Images Containing Both Bone and Iodine", Oct. 1997.

J. Hsieh, Medical Ct and Ultrasound: Current Technology and Application, XP–009011602, pp. 487–518, "Image Artifacts, Causes, and Correction", 1995.

* cited by examiner

*Primary Examiner*—David V Bruce
(74) *Attorney, Agent, or Firm*—Oblon, Spivak, McClelland, Maier & Neustadt, P.C.

(57) ABSTRACT

An image processing apparatus is provided for processing a plurality of sets of projection data acquired by radiating an X-ray onto an object in a multitude of directions. The apparatus has a correcting unit and a reconstructing unit. The correcting unit corrects the projection data with regard to beam hardening of the projection data. The beam hardening is caused due to a contrast agent injected into the object. For example, the correcting unit includes a correction table defining a correcting value to a change in densities of a region in which the contrast agent is present and corrects the projection data on the basis of the correcting value obtained from the correction table. The reconstructing unit reconstructs the corrected projection data into an image of the object. Thus, artifacts due to beam hardening resultant from use of the contrast agent can be avoided.

11 Claims, 12 Drawing Sheets

IMAGE PROCESSING INVOLVING CORRECTION OF BEAM HARDENING

BACKGROUND OF THE INVENTION

1. Technical Field of the Invention

The present invention relates to an image processing apparatus and a medical imaging modality, both of which provide images of the internal structure of an object to be examined, and in particular, to the apparatus and modality capable of correcting beam hardening caused due to a contrast agent injected into the object.

2. Description of Related Art

As one conventional medical modality, there have been known modalities to obtain contrast-enhanced blood vessel images using a contrast agent. Such modalities include an X-ray imaging system directed to circulatory organs. The X-ray imaging system is equipped with, for example, an approximately C-shaped supporter (hereafter, referred to as a "C-shaped arm"), an X-ray tube, functioning as an X-ray generator, attached to one end of the C-shaped arm, an image intensifier, functioning as a detector, attached to the other end of the C-shaped arm, an image processor for processing acquired projection data, and other components. This system is also called an X-ray angiography system, and it enables X-ray imaging conducted during examination and operations, such as insertion of a catheter into an object, carried out by a doctor.

Another medical modality has been proposed as an IVR (Interventional Radiology)-CT system in which the foregoing X-ray angiography system and an X-ray CT scanner are incorporated in a combined manner. In this IVR-CT system, the CT gantry of the X-ray CT scanner and the C-shaped arm of the X-ray angiography system are operated in a mutually-related manner in the same diagnostic spacing. For instance, information about an object (which is for example a tomographic image or a blood vessel contrasted image) acquired by one of the systems is used to determine in a shorter period of time how to perform an X-ray examination in charge of the other system. Therefore, on inserting a catheter into a region to be examined of an object, it is possible to perform entire angiographic imaging, then to perform CT imaging to determine nutrient blood vessels to a tumor.

This IVR-CT system makes it possible to perform IVR. That is, an aneurysm, constriction and others are treated through surgery in a lower-degree invasiveness, under an X-ray fluoroscopic condition. In the IVR, a catheter is inserted to a portion to be examined. And if there is an aneurysm in the portion, a coil ejected from the tip of the catheter is placed within the aneurysm, while if a constriction is present in the examined portion, a balloon is loaded to be ejected and expanded in the constriction.

For conducting such operational techniques, it is extremely significant that blood vessels in a region being examined of an object are three-dimensionally grasped. The foregoing X-ray angiography system makes it possible to reconstruct a three-dimensional vessel structure from contrasted images obtained during operations. Hence 3D imaging based on the X-ray angiography system recently has become an indispensable tool for the IYR.

However, in such 3D imaging based on the angiography system that uses a contrast agent, there is a problem of artifacts caused in connection with blood vessels. In other words, when acquiring signals of a blood vessel running in a certain direction and reconstructing the image thereof, an angiographic image R1, which should be displayed originally, is deformed into a more compressed angiographic image R2, as shown in FIG. 1A. This compression problem becomes more noticeable when the foregoing "certain direction" agrees with a direction in which an X-ray path (X-ray transmittance length) becomes longer especially.

As to the 3D imaging based on the angiography system, there is another problem. To be specific, for imaging an aneurysm having a larger diameter as shown in FIG. 1B, reconstructed values at pixels residing within the aneurysm itself are likely to reduce. If such a phenomenon occurs, a certain inner area of an aneurysm is displayed without pixel values, that is, in a hollow state. Concurrently with this, other blood vessels that run around the aneurysm are displayed thinner than their true diameters.

It is considered that the primary cause comes from the fact that the X-ray provides X-ray multiple spectrums. That is, the cause is considered one type of beam hardening phenomenon, in which projection data based on a specific region of the X-ray spectrums that contributes largely to the absorption of a contrast agent decrease greater compared to projection data based on the remaining region of the X-ray spectrums. In general, concerning this beam hardening toward such elements as bones and soft tissues, a variety of types of correction techniques have been proposed. However, no correction techniques have been reported yet toward artifacts caused by the contrast agent.

An examination that uses a contrast agent is also carried out by the X-ray CT scanner and is called CTA (Computed tomographic angiography). The CTA uses a contrast agent which is injected from a vain. The density of such contrast agent is as small as approximately $\frac{1}{10}$, compared to that of a contrast agent that is directly administered from an artery.

Incidentally, strictly speaking, the term "densities" used in this specification means a product of the density itself of an injected contrast agent and a thickness of an area (pixels) in which the contrast agent is present. Provided that the density of the injected contrast agent is constant, the "densities" correspond to a thickness of the area. It is therefore possible the "densities" can be interpreted as pixel values.

The X-ray CT scanner has therefore no problems about foregoing artifacts, because a lower-density contrast agent is used. In contrast, in the case of the X-ray angiography system, a catheter is inserted to a portion to be examined under a fluoroscopic condition in order to directly inject the contrast agent into the examined portion. Thus, a contrast agent is injected before its densities begin to decrease, so that the higher-density contrast agent often causes artifacts as described above, although such higher-density contrast agent is helpful in obtaining highly contrasted images.

Like the above, the IVR-CT system allows a doctor to inject a higher-density contrast agent from a catheter placed near to a portion to be examined, thus encountering the similar artifact problem as the above.

SUMMARY OF THE INVENTION

The present invention has been performed in consideration of the foregoing drawbacks. An object of the present invention is to provide both of an image processing apparatus and a medical imaging modality, which are able to prevent artifacts that appear on blood vessel images and images of an aneurysm or others on account of beam hardening caused by a contrast agent administered into an object.

In order to realize the above object, as one aspect of the present invention, there is provided an image processing apparatus for processing a plurality of sets of projection data to visualize an internal structure of an object to be imaged, the plurality of sets of projection data being acquired by radiating an X-ray onto the object in a multitude of directions, the apparatus comprising: a correcting unit configured to correct the projection data with regard to beam hardening of the projection data, the beam hardening being caused due to a contrast agent injected into the object; and a reconstructing unit configured to reconstruct the corrected projection data into an image of the object.

The projection data suffered from beam hardening caused due to the contrast agent injected into the object is corrected in a steady manner, before being reconstructed into an image. Accordingly, various artifacts, such as compressing angiographic images and disappearances of values of pixels residing in an inner area of an aneurysm, that is, a hollow-state display, can be avoided with steadiness. Since such artifacts are greatly diminished or removed, automatic measurement of the size of a region including such blood vessels can be preformed with reliability.

It is preferred that the correcting unit includes a correction table defining a correcting value to a change in densities of a region in which the contrast agent is present and correcting means configured to correct the projection data on the basis of the correcting value obtained from the correction table.

It is also preferred that the correction table consists of a plurality of correction tables each formed correspondingly to each of different X-ray tube voltages and selects any of the plurality of correction tables in response to a specified X-ray tube voltage.

Still preferably, the image processing apparatus further comprising a processing unit configured to calculate a subtraction value, pixel by pixel, between two sets of the projection data acquired in each direction before and after injecting the contrast agent, wherein the correcting unit includes a correction table defining a correcting value for the subtraction value to a change in densities of a region in which the contrast agent is present and calculating means configured to correct the projection data based on the correcting value obtained from the correction table. As a result, the beam-hardening correction can also be applied to digital subtraction angiography.

It is also preferred that the image processing apparatus further comprises: an extracting unit configured to extract, from the image reconstructed by the reconstructing unit by the use of the projection data acquired after injecting the contrast agent, the region in which the contrast agent is present, on the basis of a predetermined threshold; and a re-projecting unit configured to re-project the extracted region in which the contrast agent is present, wherein the correcting unit including correcting means for correcting projection data re-projected by the re-projecting unit on the basis of the correction table; and the reconstructing unit including reconstructing means for reconstructing again the re-projected data corrected by the correcting unit.

In this way, the reconstruction processing is carried out twice with the correction process toward the beam hardening placed therebetween two times of reconstruction steps. It is therefore possible to remove artifacts on account of the contrast agent injected.

It may also be possible that the image processing apparatus further comprises: an extracting unit configured to extract, from the image reconstructed by the reconstructing unit with by the use of the projection data acquired after injecting the contrast agent, each of the region in which the contrast agent is present, a region of a bone, and a region of a soft tissue, on the basis of each threshold assigned to each of the regions; and a re-projecting unit configured to re-project each of the extracted regions; wherein the correcting unit including the correction table consisting of a plurality of correction tables each formed correspondingly to each region, correcting means for correcting, region by region, projection data re-projected by the re-projecting unit on the basis of each of the correction tables, and combining means for combining the re-projected data of each region with each other to form projection data again; and the reconstructing unit including reconstructing means for reconstructing again the projection data combined by the combining unit.

In order to achieve the foregoing object, as another aspect of the present invention, there is provided a medical imaging modality comprising a data acquiring unit including a device for generating an X-ray and a device for detecting the X-ray, both devices being supported face to face by a supporter so that projection data composed of X-ray transmittance data mapped at each pixel are acquired for imaging, an object being imaged being placed between the devices; a processing unit configured to calculate a subtraction value, pixel by pixel, between the projection data acquired before injecting a contrast agent into the object and the projection data acquired after injecting the contrast agent the object; a correcting unit configured to correct the projection data with regard to beam hardening of the projection data, the beam hardening being caused due to the contrast agent injected into the object; and a reconstructing unit configured to reconstruct the corrected projection data into an image of the object.

Preferably, the correcting unit includes a correction table defining a correcting value to a change in densities of a region in which the contrast agent is present and correcting means configured to correct the projection data on the basis of the correcting value obtained from the correction table.

It is also preferred that the supporter is an arm member approximately formed into a C-shape and formed to support both the devices mounted on both ends thereof.

In order to achieve the foregoing object, as another aspect of the present invention, there is provided a medical imaging modality comprising a data acquiring unit including a device for generating an X-ray and a device for detecting the X-ray, both devices being supported face to face by a supporter so that projection data composed of X-ray transmittance data mapped at each pixel are acquired for imaging, an object being imaged being placed between the devices; a first reconstructing unit configured to reconstruct an image of the object from the projection data acquired by a plurality of sets after injecting the contrast agent; an extracting unit configured to extract a region in which the contrast agent is present, from the image reconstructed by the first reconstructing unit on the basis of a predetermined threshold; a projecting unit configured to re-project the extracted region; a correcting unit configured to correct the re-projected data with regard to beam hardening of the projection data, the beam hardening being caused due to the contrast agent injected into the object; and a second reconstructing unit configured to reconstruct the corrected re-projected data into a further image of the object.

DETAILED DESCRIPTION OF PREFERRED EMBODIMENTS

Hereinafter, with reference to the accompanying drawings, embodiments of the present invention will now be described in detail.

First Embodiment

Referring to FIGS. 2 to 6, a first embodiment of the medical modality according to the present invention will now be described, in which the image processing apparatus of the present invention is functionally incorporated in the imaging modality. In this first embodiment, the medical modality is reduced into practice as a three-dimensional (3D) angiography system.

The 3D-angiography system according to the present embodiment is able to perform processing including the production of images on the basis of two modes consisting of a DA (Digital angiography) mode and a DSA (Digital Subtraction Angiography) mode. The DA mode allows the system to perform X-ray imaging with a contrast agent to acquire an X-ray image that includes flows of the contrast agent administered into an object and to display and store the acquired image. On the other hand, under the DSA mode, both of an X-ray mask image acquired without injecting a contrast agent and an X-ray image (contrast-enhanced image or live image) that includes flows of a contrast agent injected into an object are subjected to subtraction to produce a subtraction image. The subtraction image, in which flows of the contrast agent are depicted more clearly than images produced under the DA mode, are displayed and/or memorized as image data. In the following, only imaging under the DSA mode will be described.

Figure 2:
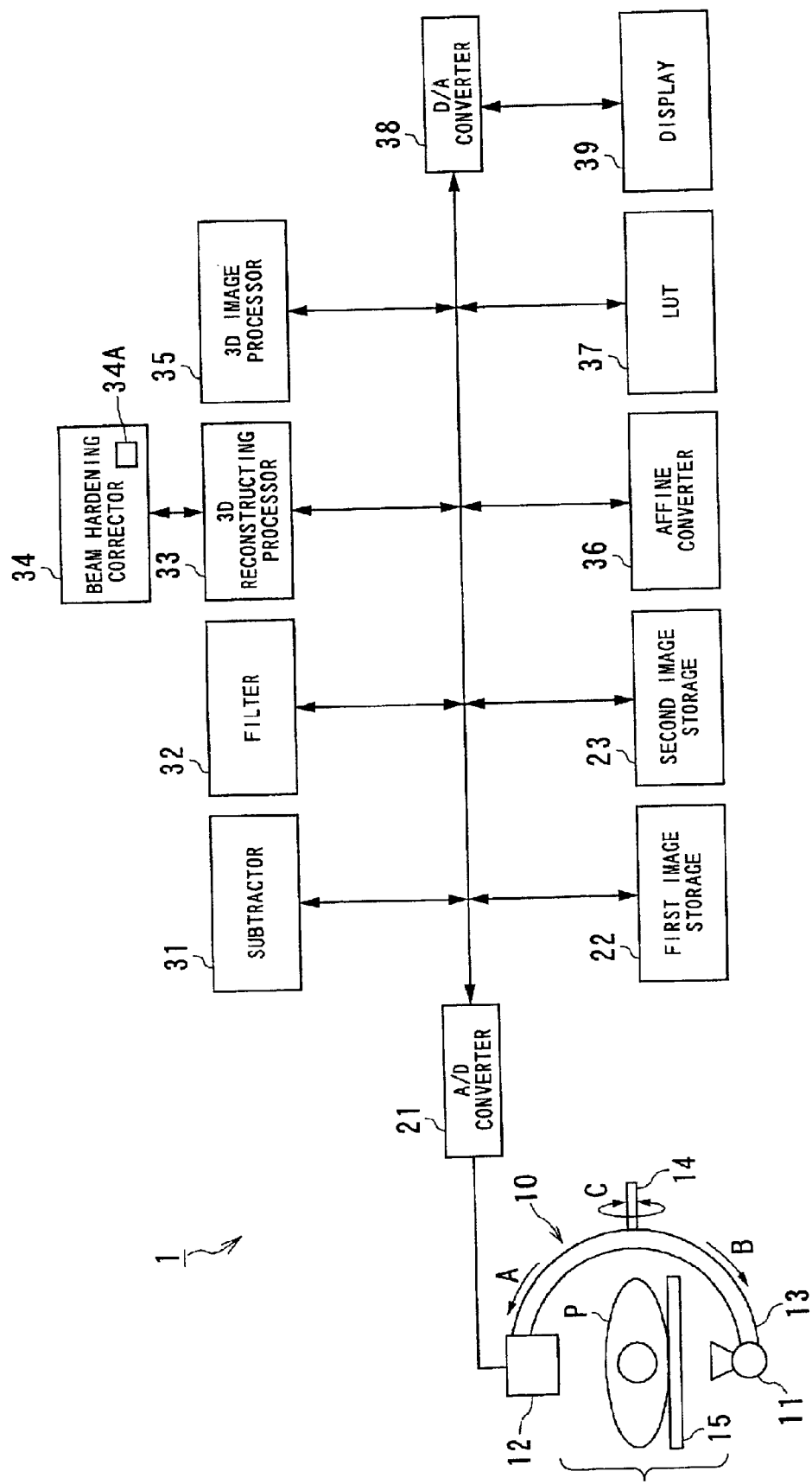
FIG. 2 is a functional block diagram exemplifying the configuration of a 3D-angiographic system serving as a first example of the medical modality according to the present invention, in which the medical modality functionally includes the image processing apparatus according to the present invention.

FIG. 2 is a functional block diagram outlining the entire configuration of the 3D-angiography system 1 according to the first embodiment. The 3D-angiography system is provided with, as shown in FIG. 2, a data acquiring apparatus 10 used for acquiring a plurality of projection data (X-ray transmission images) through X-ray radiation in a multitude of directions (imaging angles) toward an object to be examined P. The 3D-angiography system is also provided with, as constituents for image processing, an A/D converter 21, first and second image storages 22 and 23, subtractor 31, filter 32, 3D-reconstucting processor 33, beam hardening corrector 34, 3D-image processor 35, affine converter 36, LUT (Look Up Table) 37 for conversion of gradations, D/A converter 38, and display 39. Although not shown, the 3D-angiography system is further provided with an X-ray control unit, a storage to store image data, an operation device used by an operator to issue desired instructions, and a controller in charge of management of the above constituents.

Of the above listed constituents, the A/D converter 21 converts X-ray data into digital amounts of signals. The first and second image storages 22 and 23 are used to memorize projection data acquired before and after the injection of a contrast agent, respectively. The subtractor 31 is responsible for subtraction between two sets of the projection data acquired in each of the same imaging angles before and after the injection of the contrast agent. The filter 32 performs various types of filtering for display, including edge enhancement and high-frequency-component enhancement. The 3D-reconstructing processor 33 carries out 3D reconstruction based on acquired projection data. The beam hardening corrector 34 is in charge of the correction of data subjected to beam hardening due to a contrast agent injected into an object P. The 3D-image processor 35 performs a variety of types of processing, such as production of image and preservation of image data. The affine converter 36 is responsible for processing including expansion, contraction, rotation, and movement of images. And the display 39 is configured to visualize images including various images acquired by the data acquiring apparatus 10, images reconstructed, and 3D images.

The controller, though not shown, is constructed such that, in replay to operations issued though the operation device, it carries out various commands of producing images and/or storing images and manages each constituent of the system. This 3D-angiography system may be provided with a pre-processor to perform proper calibrating correction such as sensitivity correction and/or X-ray intensity correction on digitized X-ray data so as to produce "projection data."

The beam hardening corrector 34 corresponds to the correcting unit of the present invention, the 3D-reconstucting processor corresponds to the reconstructing unit of the present invention, and the subtractor 31 corresponds to the processing unit of the present invention.

As shown in FIG. 2, the data acquiring apparatus 10 includes an X-ray tube 11 in which an X-ray source (not shown) is contained and an X-ray detector 12 formed by for example an image intensifier (I.I.). Both of the X-ray tube 12 and the X-ray detector 12 are mounted on both ends of a C-shaped arm also included in the apparatus 10. This apparatus 10 is also provided with a patient couch 15 on which a patient (object to be examined) is laid. The C-shaped arm can be slid, as shown by arrows A and B in FIG. 2, so as to lift the X-ray tube 11 from under the couch 15 upward left in FIG. 2 or to move the X-ray detector 12 over the patient P. In addition, the C-shaped arm can be rotated by its rotation shaft 14, as shown by an arrow C in FIG. 2. In order to realize the movements shown by the arrows A, B and C, the C-arm 13 is coupled with both of a plurality of power sources and arm-state detecting means (not shown) to detect angles and positions thereof supplied as detected signals to the power sources.

The 3D reconstructing processor 33 includes a distortion correcting unit to correct distortions of the I.I. and others and an inversely projecting unit, thought both of which are not shown.

As easily understood from the outer form of the C-shaped arm 13, the 3D angiography system 1 allows a doctor or other operators to easily access the patient C from an opening formed between both the ends of the C-shaped arm 13. This is different from that given by the X-ray CT system of which gantry is totally around a patient. Thus, in the case of this 3D angiography system 1, a doctor who gained access to the patient P from the opening of the arm 13 is able to perform operations or examination, such as an insertion of a catheter, during which time the doctor is also able to conduct X-ray angiography with a contrast agent. Thus the 3D-angiography system 1 is best suitable for IVR, which enables complicated inserting operations of a catheter.

The foregoing constituents from the data acquiring apparatus 10 to the display 39 permit the X-ray detector 12 to detect an X-ray that passed the patient P after the radiation from the X-ray tube 11 and to process the detected X-ray data in a predetermined proper manner. Thus, a variety of images can be produced and displayed for observation. For instance, a pulsed X-ray of a lower level is continuously radiated from the X-ray tube 11 and its continuously transmitted X-ray is detected by the X-ray detector 12. This way of imaging provides fluoroscopic images of the patient P. Alternatively, the C-arm 13 is rotated around the patient P during which time projection data is acquired in a plurality of directions each passing the patient P. This way of scanning provides tomographic images of the patient P. In addition, the system 1 allows three-dimensional images of the patient P to be produced as well.

Practically, an electric motor (not shown) mounted on a base of the 3D angiography system 1 is driven such that the C-shaped arm 13 is rotated, in a shorter period of time, through an angular range of more than 200 degrees around the patient P, during which time raw data is acquired in each imaging direction passing the patient P. That is, while the C-shaped arm 13 is rotated in either direction shown by the arrows C (i.e., while imaging angles are changed), the imaging is repeated at angular intervals of 1 degree. Hence X-ray intensity distributions for 200 degrees, that is, for changed rotation angles, are collected. This provides 200-pattern X-ray intensity distributions (projection data), which are then converted into digital signals by the A/D converter 21.

By way of example, when reconstructing an image depicting only blood vessels, the foregoing acquisition of projection data is carried out twice, before and after the injection of a contrast agent. The projection data acquired before the injection is stored into the first image storage 22, whilst those acquired after the injection is stored into the second image storage 23. After storing such projection data into the storages 22 and 23, the processing of subtractor 31 is activated so as to perform subtraction (DSA: Digital Subtraction Angiography) processing. In other words, the subtraction is carried out for every the same imaging angle, between an image (mask image) acquired before the injection of a contrast argent and an image (contrasted image) acquired after the injection thereof. The projection data that undergoes the subtraction is sent to the 3D-reconstructing processor 33.

The above subtraction should be done between the mask and contrasted images both acquired at the same angular position. It is thus necessary to have positional coordinates showing both the images. A subtraction image is therefore produced when the positional coordinates of both images agree with each other. This "agreement" is automatically processed such that the system 1 recognizes a position (positional coordinates) of each mask image to acquire a contrasted image at the recognized position.

The reconstruction processing carried out by the 3D reconstructing processor 33 is assigned to a discrete reconstruction region. One example of the reconstruction techniques is a filtered back projection (filter inverse projection) proposed by "Feldkamp et al." In this technique, the filter 32 is activated for convolution by applying a properly selected convolution filter (correction filter) to the produced 200-frame DSA image data (projection data). For example, the convolution filter is proposed by "Sheep & Logan" and "Ramachandran."

The 3D reconstructing processor 33 performs inverse projection processing on the convoluted projection data, thereby providing 3D reconstructed image data. The reconstructed 3D image data is then stored into the storage, before completing the reconstruction.

Alternatively, the 3D reconstructing processor 33 may be constructed to include a distortion-correcting unit (not shown) to correct distortions of projection data suffered from the image intensifier. After this correction, the filter 32 may apply a correction filter according to the filtered back projection technique to the DSA image data (projection data), with the convolution performed. Moreover, in the configuration with no image intensifier serving as the X-ray detector, such distortion-correcting unit is unnecessary. The X-ray detector may be a planar type of X-ray detector, called "FPD (Flat panel Detector), in place of the image intensifier.

A region to be reconstructed can be defined as a cylindrical region inscribing a flux of X-rays in all the directions from the X-ray tube 11. The cylindrical region is made to be discrete three-dimensionally with a length, at the position of the central axis of the region, projected to the width of one detecting element of the X-ray detector 12. Data acquired from the discrete positions are used to reconstruct an image. The discrete intervals are not limited to the above, but other intervals can be adopted. In some cases, the discrete intervals depend on system configurations, and in such a case, discrete intervals determined by a system configuration are used.

Thus, the region to be reconstructed is converted three-dimensionally into grids, called voxels. Each of the voxels provides one piece of data, so the entire voxels provide three-dimensional discrete data.

An image, such as a tomographic image of the object P, which has been obtained by the reconstruction in the 3D reconstructing processor 33, is then subjected to various types of processing including discrimination with a threshold in order to extract a region of blood vessels. Such various types of processing further include shading processing for shading the surfaces of the blood vessels. After such types of processing, a surface image of the blood vessels viewed along a certain direction can be displayed.

After completing the reconstruction of a 3D image, a signal indicating that the 3D image is displayable is sent to the display 39. In response to the signal, the display 39 operates so as to display the 3D image using one selected from a variety of 3D-image displaying techniques, which include a volume rendering technique, surface rendering technique, MIP (Maximum Intensity Projection) technique, MinIP (Minimum Intensity Projection) technique, and X-ray projection technique. For displaying the 3D image, it is possible to change various parameters, such as an optical parameter converting function (in the case that the surface rendering technique is adopted, such function is composed of thresholds), color, the position of a light source, and intensity. It is preferable that the selection of any 3D-image displaying technique and control of such parameters for the 3D display are determined beforehand as default values, before being subjected to operator's arbitrary selection and control, if needed.

The LUT 37 and filter 32 are used, if needed, when the above 3D image and/or its original DSA image are further processed into images which make it easier to observe the images for diagnosis.

Correction of Beam Hardening

Figure 3A:
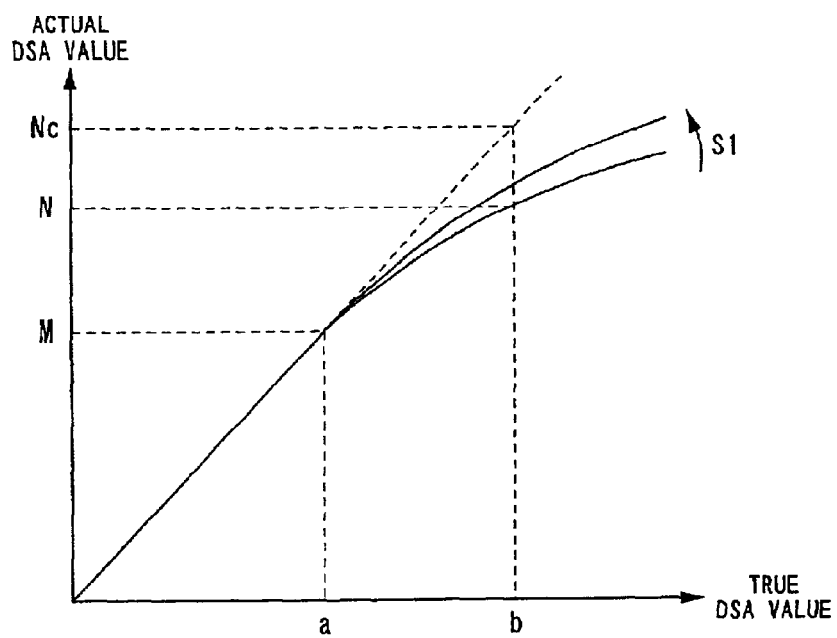
FIGS. 3A and 3B explain one example of a correction table used in the angiography system.
Figure 3B:
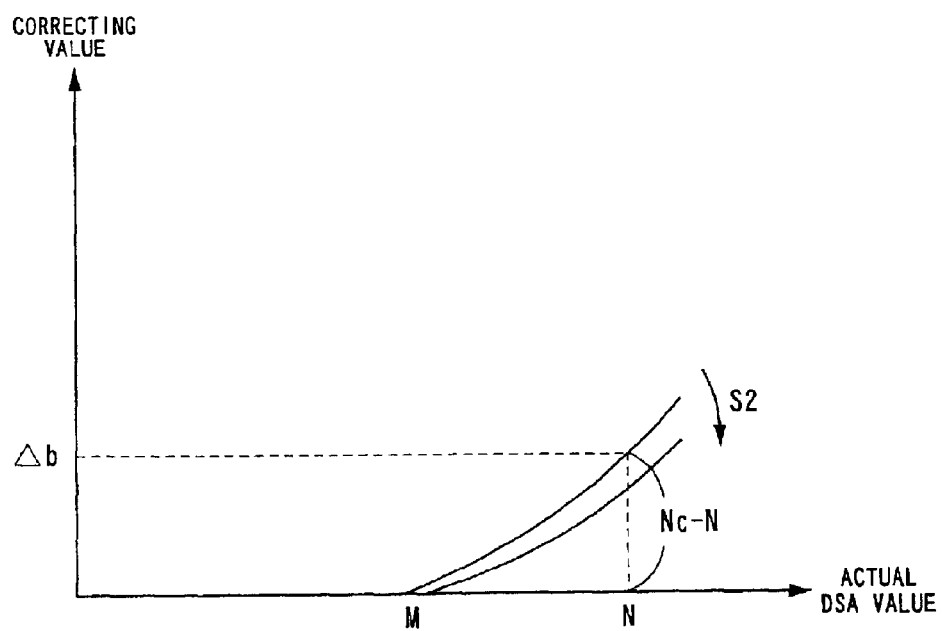
Figure 4:
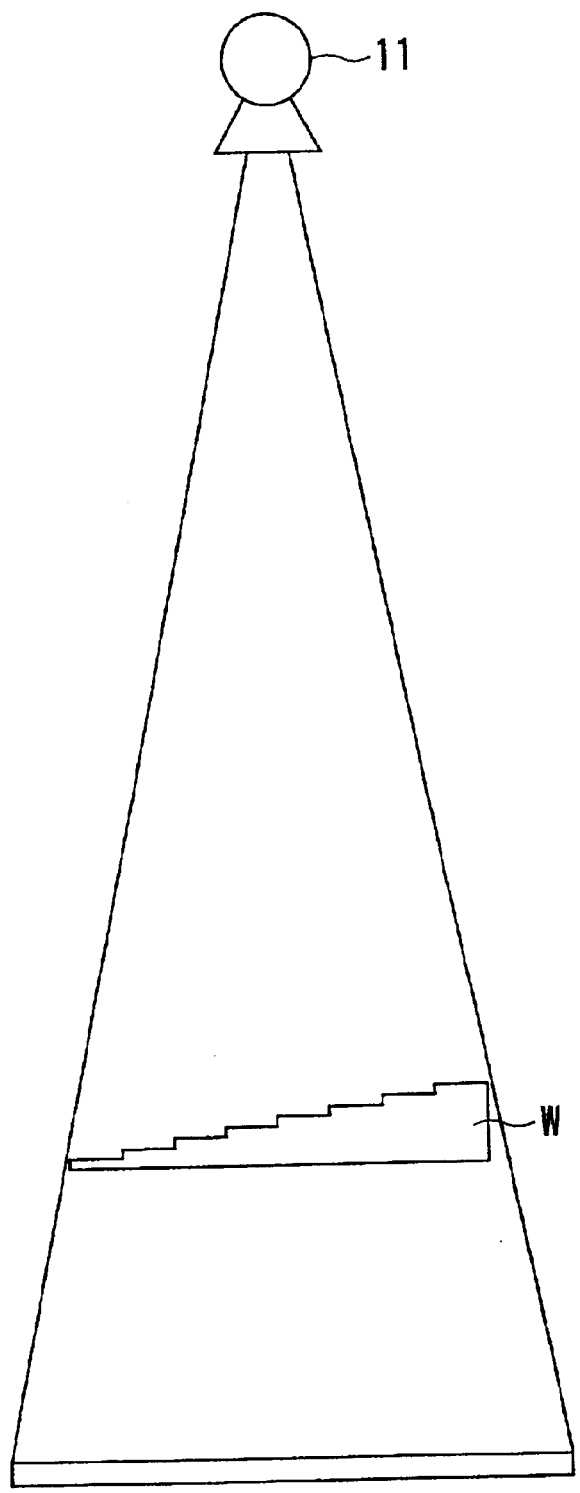
FIG. 4 is an illustration of an experimental system for acquiring data used to produce the correction table.

Referring to FIGS. 3 and 4, the correction of beam hardening, which is an essential feature of the present invention, will now be detained described.

The beam hardening corrector 34 is placed to correct the beam-hardening phenomenon caused primarily by a contrast agent injected into an object. A correction table 34A, which is stored in the beam hardening correlator 34, defining the correlation relationship between actual DSA values and correcting values as shown in FIG. 3B, is used to correct the actual DAS values.

For example, as shown in FIG. 3A, a true DSA value of b corresponds to an actual DSA value of N, thus, as shown in FIG. 3B, corresponding to a correcting value of b. Therefore, the correcting value of b is used to convert a corrected DSA value to "N+b."

The correcting values are derived as follows. An experimental configuration to measure the correcting values is made, wherein the X-ray tube 11, the X-ray detector 12, and a member W with which a contrast agent is filled. The contrast agent member W though which an X-ray path passes is changed in densities stepwise. The density of the contrast agent is constant. Actual DSA values (i.e., subtraction values between projection data with and without a contrast agent) are calculated. Then, as shown in FIG. 3A, the actual DSA values are plotted against the known true DSA values.

As understood from curves plotted in FIG. 3A, within a range whose true DSA values are equal or less than a value of a actual DSA values increase linearly, as the contrast agent member W increases in densities. However, in the remaining range whose true DSA values are over a value of a, the curve shows a non-linear characteristic so that the rate of increase is lowered gradually. This phenomenon is caused by the fact that the X-ray spectrum actually consists of a multiple of spectrums. In cases where an X-ray passes a contrast agent member of a certain densities or more, projection data of which X-ray spectrums falling into a specific spectrum range contributing largely to absorption of the contrast agent is reduced greater than projection data of which X-ray spectrums falling into the remaining spectrum range. In other words, from an apparent point of view, the X-ray absorption rate is relatively lowered. As a result, in a region of which contrast agent is thicker, the absorption rates of X-ray spectrums are regarded as being lower than their actual absorption rates. For example, when a true DSA value is b, an actual DSA value would be Nc, as long as the absorption rate changes in a linear manner. However, because of the above stated reason, an actual DSA value is obliged to be N. The correcting value $\Delta b$ becomes $\Delta b = Nc - N$.

Through this experiment, as shown in FIG. 3A, the actual DSA values to the true DSA values can be measured. The measurement values are then used to obtain the correcting values, thus being converted into the correlation relationship between the actual DSA values and the correcting values, as shown in FIG. 3B. The correction table 34A that defines such correlation relationship is prepared beforehand. Making reference to the correction table 34A makes it possible to have a value (DSA value) at each pixel of an acquired image that was acquired is obtained. By adding the obtained correcting value to the actual DSA value, influences of beam hardening can be eliminated or suppressed remarkably.

The correlation characteristic shown in FIG. 3A depends, in the rate of changes, on voltage applied to the X-ray tube. Hence it is preferred that the correction table 34A is prepared for each X-ray tube voltage, thus a plurality of correction tables 34A being prepared. The higher the tube voltage, the less the influences of beam hardening. The correlation characteristics are thus changed as shown by an arrow S1 in FIG. 3A, when the tube voltage is raised. Those changes are reflected in FIG. 3B, as shown by an arrow S2; that is, as the tube voltage is raised, the correcting amounts b are lowered. Preferably, the beam hardening corrector 34 is configured in such a manner that it selects, from a plurality of correction tables 34A previously prepared correspondingly to each X-ray tube voltage, a corresponding one correction table 34A to a specified X-ray tube voltage. This selection is realized by providing the beam hardening corrector 34 with a function of selecting a given correction table 34A by using tube voltage information included in attached information.

Additionally, in the 3D reconstructing processor 33, it is preferable to correct distortions. For the sake of an easier understanding, the correction of distortions may be considered using a phantom consisting of a plurality of wires arranged at equal intervals to form a square grid pattern. When carrying out imaging with the image intensifier (I.I.) on front of which the above phantom is placed, a square grid-like projection image shown in FIG. 5A should be gained, provided that there are no distortions in the image intensifier. However, practical image intensifiers suffer from spool-shaped distortions resultant from their frontal shapes and/or S-shaped distortions on account of earth magnetism. Such distortions result in a projection image shown in FIG. 5B.

Figure 5A:
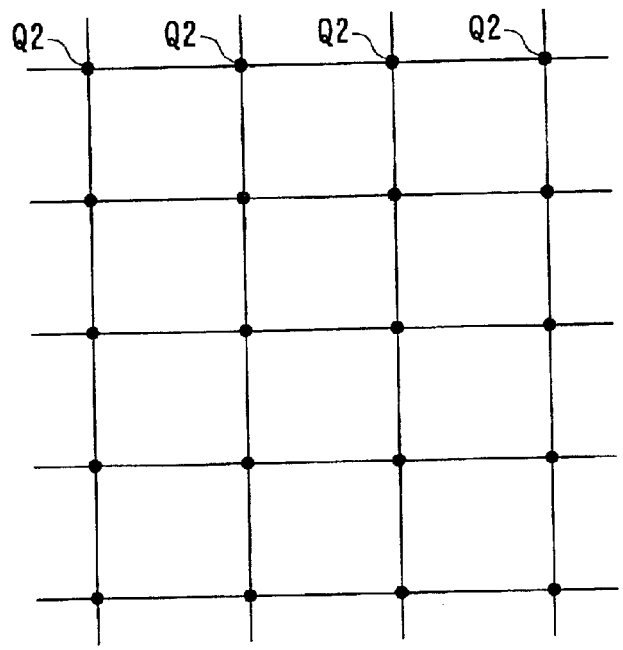
FIGS. 5A and 5B are illustrations for expanding the principle for correcting distortions.
Figure 5B:
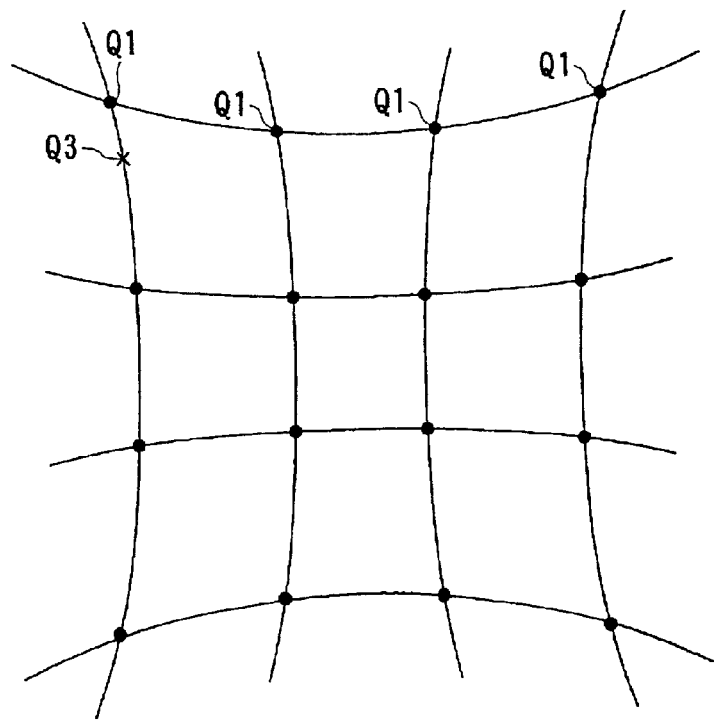

To remove or suppress such influences of the distortions, the data of a distorted projection image, as shown in FIG. 5B, are previously collected, and the collected data are used to extract each grid point Q1 (i.e., grid-point information) at which both wires intersect. As long as there are no distortions, the grid points Q1 should be at equal intervals on a straight line, like grid points Q2 as shown in FIG. 5A. Therefore, at first, correction is performed to convert a series of grid points Q1 to a straight line on which the grid points Q2 exist at equal intervals (correction of the grid points). Other points, for example, Q3, other than the grid points Q1, are estimated using a proper approximation technique involving the grid-point information about surrounding grid points Q1. That is, such points other than the grid points Q1 are also corrected from the surrounding square grid points (correction of other points), thereby completing the correction of the distortions. In addition, since the distributions of distortions depend on imaging angles, distortion-distributing tables, each of which is measured from each phantom projection image acquired at each imaging angle, are held. Accordingly, the distortions are corrected using the distortion-distributing tables.

Processing Procedures

Referring to a flowchart shown in FIG. 6, the entire operations and advantages of the above 3D-angiography system 1 will now be described. This description will be spotlighted onto the correction of beam hardening according to the present invention.

Figure 6:
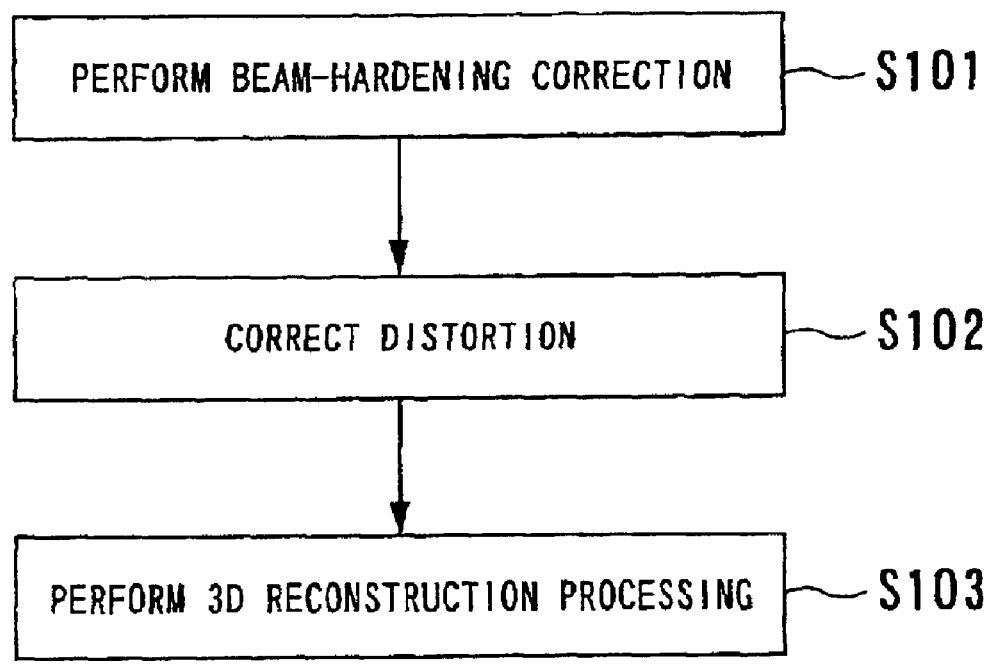
FIG. 6 is a flowchart outlining part of a series of procedures of processing carried out by the angiography system.

After the subtraction processing, the correction of beam hardening due to an injected contrast agent into an object P is activated (step S101 in FIG. 6).

At step S101, the beam hardening corrector 34 shown in FIG. 2 makes reference to the correction table 34A in which the correlation relationship shown in FIG. 3B is written and corrects the DSA values. For example, if a true DSA value is b, as shown in FIG. 3A, the corrector 34 calculates a correcting value of b by referencing the correction table 34A and corrects the actual DSA value to "N+b." In this way, the DSA values of an acquired image are subjected, pixel by pixel, to the correction of the beam hardening according to the correction table 34A. The influences of the beam hardening, which is caused by various densities in areas where the contrast agent exist, can therefore be suppressed or eliminated.

Furthermore, in this embodiment, the correction table 34A is prepared for each amount of voltage to be applied to the X-ray tube. The beam hardening corrector 34 is configured to select the most suitable correction table 34A according to a specified certain X-ray tube voltage, and then to compute the corrected DSA values on the basis of the selected correction table 34A. Hence the influences of the beam-hardening phenomenon due to the contrast agent can be corrected in consideration of the effects resultant from differences in voltage to be applied to the X-ray tube.

Returning to the description of FIG. 6, the distortions due to the image intensifier is corrected (step S102). At this step S102, referencing projection image data collected in advance, which can be exemplified as shown in FIG. 5B, is used by the 3D reconstructing processor 33 such that the referencing projection image data is looked up to compute the grid points Q1 (grid-point information) at each of which wires intersect to each other.

The 3D reconstructing processor 33 then corrects the grid points Q1 (refer to FIG. 5B) so as to be equal in intervals like the grid points Q2 (refer to FIG. 5A) (i.e., correction of the grid points). Based on the grid-point information about each grid point Q1 residing around each point Q3 other than grid points Q1, the processor 33 then computes a position corresponding to that of a square grid shown in FIG. 5A, thereby correcting each point Q3 (correction of other points). Making reference to each of the distortion distributing tables measured using the foregoing phantom projection images leads to such correction of distortions. Thus the distortions can be corrected by taking into account spool-shaped distortions due to the shape of the X-ray incidence surface of the image intensifier and S-shaped distortions due to earth's magnetism and other factors.

Returning to FIG. 6 again, the three-dimensional reconstruction is performed by the 3D reconstructing processor 33 (step S103). By way of example, when the filtered back projection technique proposed by Feldkamp et al., the processor 33 applies a convolution filter to a frame of DSA image data (projection data). Then the 3D reconstructing processor 33 calculates three-dimensional inverse projections toward the filtered data of a DSA image, thereby providing reconstructed 3D image data.

The reconstructed 3D image data are sent to the display 39, in which the data are three-dimensionally visualized through, for example, a volume rendering technique.

As described above, according to the present embodiment, DSA data is subjected to reconstruction processing, so that a subtraction image depicting only blood vessels is obtained.

For producing such subtraction images, changes in DAS value v.s. changes in densities of areas in which a contrast agent is present are held as reference correction tables 34A in advance. Hence, acquired DSA values are made to look up into the reference correction tables 34A, so that the acquired DSA values are corrected into a linear correlation relationship between the actual and real DSA values. The corrected DSA data then undergoes reconstruction processing into an image. Accordingly, regardless of densities and amounts of a contrast agent, it is possible to eliminate or suppress artifacts to be brought by the beam-hardening phenomenon due to the contrast agent injected into an object. In particular, the original shapes of blood vessels that run in directions perpendicular to the rotation shaft of the C-shaped arm are also depicted in an exact manner.

Figure 1A:
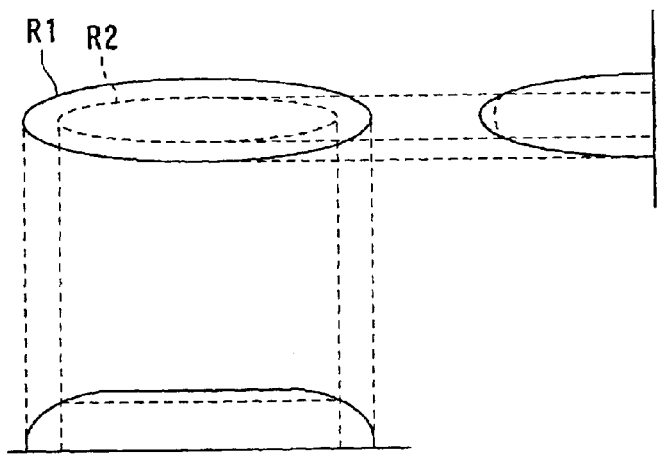
FIGS. 1A and 1B are illustrations to show artifacts caused in association with the conventional techniques.
Figure 1B:
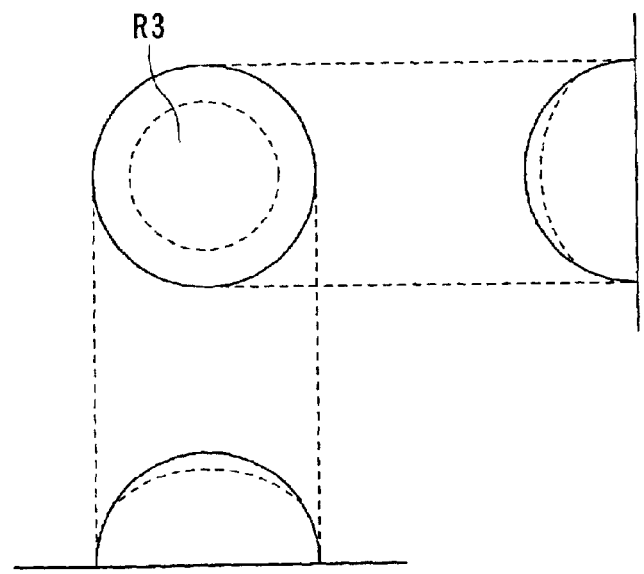

Therefore, the foregoing various artifacts, such as compressing angiographic images (refer to FIG. 1A) and drops of values at pixels residing in an inner area of an aneurysm, that is, a hollow-state display (refer to FIG. 1B), can be avoided with steadiness. In general, recent medical diagnostic imaging modalities have a function of automatically measuring the size of a region (area of volume) of interest by using a given threshold assigned to the pixel values. If blood vessels are deformed in their shape or there are no pixel values in a certain inner area of the aneurysm, the measurement of the region size would be erroneous, thus spoiling the measurement in reliability. In contrast, since such artifacts are greatly diminished or removed in the present embodiment, the measurement can be preformed with reliability.

The present embodiment has described the 3D angiography system in which the 3D reconstructing processor 33, beam hardening corrector 34, and 3D image processor 35, which compose the image processing apparatus, are united with the constituents for X-ray imaging. An alternative configuration is one in which such constituents 33 to 35 that compose the image processing apparatus may be separated physically from the 3D angiography system itself.

Second Embodiment

A second embodiment of the present invention will now be described. In the following, the constituents substantially similar or identical to those in the first embodiment will be omitted from the description, only different constituents being described.

In the first embodiment, the beam-hardening phenomenon has been corrected using the plural correction tables 34A each of which memorizes correction data collected to each value of voltage to be applied to the X-ray tube. Instead of this, the second embodiment adopts a correction table memorizing correction data that is set to only a representative of a certain range of voltages to be applied to the X-ray tube.

Practically, the beam hardening corrector 34 shown in FIG. 2 is configured so that it has a correction table 34A that memorizes correcting data that is set to only a representative voltage selected from a certain range of voltages to be applied to the X-ray tube. In this case, however, it is required that the voltage of the X-ray tube is changed within a smaller range of voltages. It is desirable that the tube voltage is changed within, for example, the range of 80±5 to ±1 keV.

In this way, in the case that the voltage of the X-ray tube is changed in a small range of voltages, correction data to each of the voltages of the X-ray tube is approximately equal to each other, or not so much difference. Hence, only a correction table 34A for a representative of those voltages is prepared, and used for the beam-hardening correction as long as the tube voltage is changed within a predetermined range. Therefore, it is possible to reduce the capacity of memories required for the correction table.

Third Embodiment

A third embodiment of the present invention will now be described, which relates to a further configuration of the correction table 34A.

Although the first embodiment takes only the influences of a contrast agent into account, some other factors, such as locations (a bone or a soft tissue), may have a large influence on measured DSA data. For example, in the case of measuring the head, its bone influences the measurement largely. By contrast, in measuring the abdomen, the soft tissue plays as an influential factor.

In the present embodiment, the beam-hardening corrector 34 shown in FIG. 2 has one or more correction tables 34A, in which correction data for the bone and/or the soft tissue, each having typical amount of densities, are stored.

The one or more correction tables 34A are divided into one for measuring the head, another for measuring the abdomen, and others, depending on which part of an object is imaged. Each of such categorized correction tables 34A is further prepared for each X-ray tube voltage. Thus, when the angiography is actually performed, DAS values acquired during the angiography are corrected by the use of the correction table 34A adaptable to both a measured region and an X-ray tube voltage.

Accordingly, the influences of the beam-hardening phenomenon can be corrected by taking it consideration both the bone and the soft tissue as well as the contrast agent.

Fourth Embodiment

Referring to FIGS. 7 to 11, a fourth embodiment of the present invention will now be described. In this embodiment, the medical modality according to the present invention is reduced into practice as an "IVR-CT system," with which the image processing apparatus according to the present invention is functionally integrated.

Figure 7:
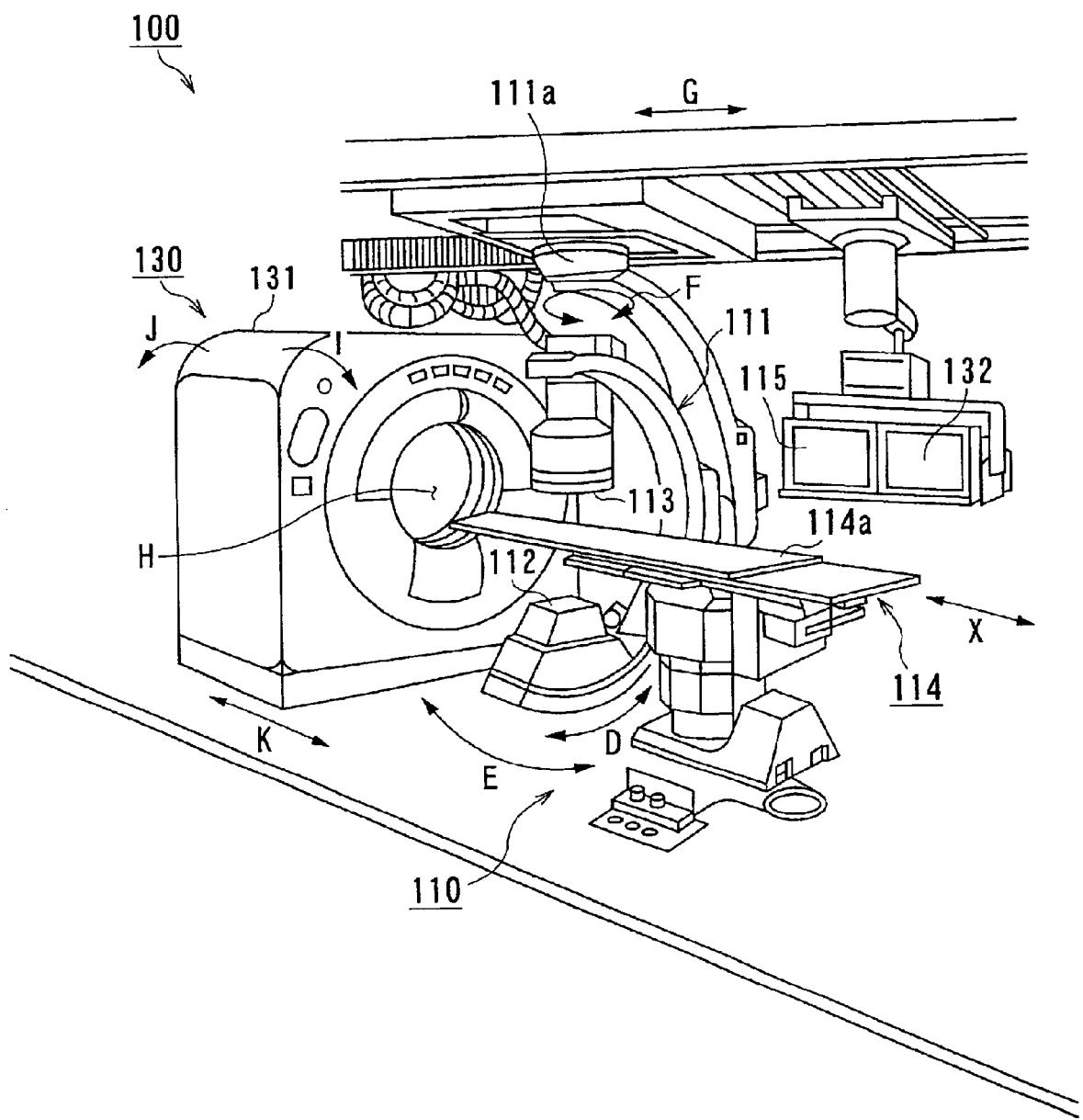
FIG. 7 is a functional block diagram exemplifying the configuration of an IVR-CT system serving as a second example of the medical modality of according to the present invention, in which the medical modality functionally includes the image processing apparatus according to the present invention.

FIG. 7 outlines the entire configuration of the IVR-CT system employed by the present embodiment. This IVR-CT system has one control system in which the control system of an ordinary angiography system and that of an X-ray CT scanner are united together.

The IVR-CT system 100 is provided with, as shown in FIG. 7, a patient couch 114 on which an object to be examined is laid, an angiography system (cardiovascular X-ray radiography system) 110 having an C-shaped arm 111, and an X-ray CT scanner (CT imager) 130 having a CT gantry 131. Of these, the C-shaped arm 111 has an approximately C-shaped arm body so that the arm body is positioned by the side of the couch 114 and moves therearound in a predetermined angular range. The CT gantry 131 has a bore (an imaging space) H, into which the tabletop 114a of the couch 114 is retractably inserted in an X-direction (corresponding to a longitudinal direction of the couch 114).

The patient couch 114 is used in common for both the angiography system 110 and the X-ray CT scanner 130. The X-ray CT scanner 130 may be composed of a spiral type of CT scanner (or referred to as a helical type of CT scanner), a dual-slice CT scanner, or a multi-slice CT scanner.

The angiography system 110 of the IVR-CT system 100 according to the present embodiment is able to perform processing including the production of images on the basis of two modes consisting of a DA (Digital angiography) mode and a DSA (Digital Subtraction Angiography) mode. The DA mode allows the system to perform ordinary X-ray radiography with a contrast agent to acquire an X-ray image that include flows of the contrast agent administered into an object and to display and store the acquired image. On the other hand, under the DSA mode, both of an X-ray mask image acquired without injecting a contrast agent and an X-ray image (contrast-enhanced image or live image) that includes flows of a contrast agent injected into an object are subjected to subtraction to produce a subtraction image. The subtraction image, in which flows of the contrast agent are depicted more clearly than images produced under the DA mode, are displayed and/or memorized as image data. In the following, only imaging under the DA mode will be described.

In the angiography system 110, on both ends of the C-shaped arm 111, an X-ray tube 112 and an X-ray detector 113 including, for example, an image intensifier (I.I.) are mounted so that they are opposed to each other. A display 115 and other components are also provided in the angiography system 110. The display 115 is in charge of visualizing images processed on the basis of projection data detected by the X-ray detector 113. Thus, a doctor is able to perform operations or examination of an object P, such as an insertion of a catheter, during which time the doctor is also able to conduct X-ray radiology to obtain angiograms with the use of a contrast agent.

The C-shaped arm 111 can be slid in directions shown by arrows D in FIG. 7, rotated in directions shown by arrows E, and pivoted in directions shown by arrows F around a fulcrum 111a. The fulcrum 111a can be traveled along directions shown by arrows G, while the C-shaped arm 111 is moved as a translation motion along the directions shown by the arrows G.

On the other hand, the X-ray CT scanner 130 includes, though not shown, an X-ray generating unit and an X-ray detector, both of which are incorporated within the CT gantry 131 so as to be rotatable around the bore H. During the rotation of both the X-ray generating unit and the X-ray detector, an X-ray irradiated from the X-ray generating unit passes the bore and is received by the X-ray detector. The scanner 130 is also provided with a display 132 to present tomographic images reconstructed by the use of signals outputted from the X-ray detector.

The CT gantry 131 can be moved to show a translation motion, as shown by arrows K in FIG. 7, so that the tabletop 114a is inserted or removed into or from the bore H of the CT gantry 131. In addition, the CT gantry 131 can be tilted in the back and forth direction, as shown by arrows J and I in FIG. 7. As a result, it is possible to control the attitudes of the CT gantry 131 in those directions, resulting in that an object P can easily be scanned obliquely to acquire DSA data from a scanned oblique tomographic plane.

Figure 8:
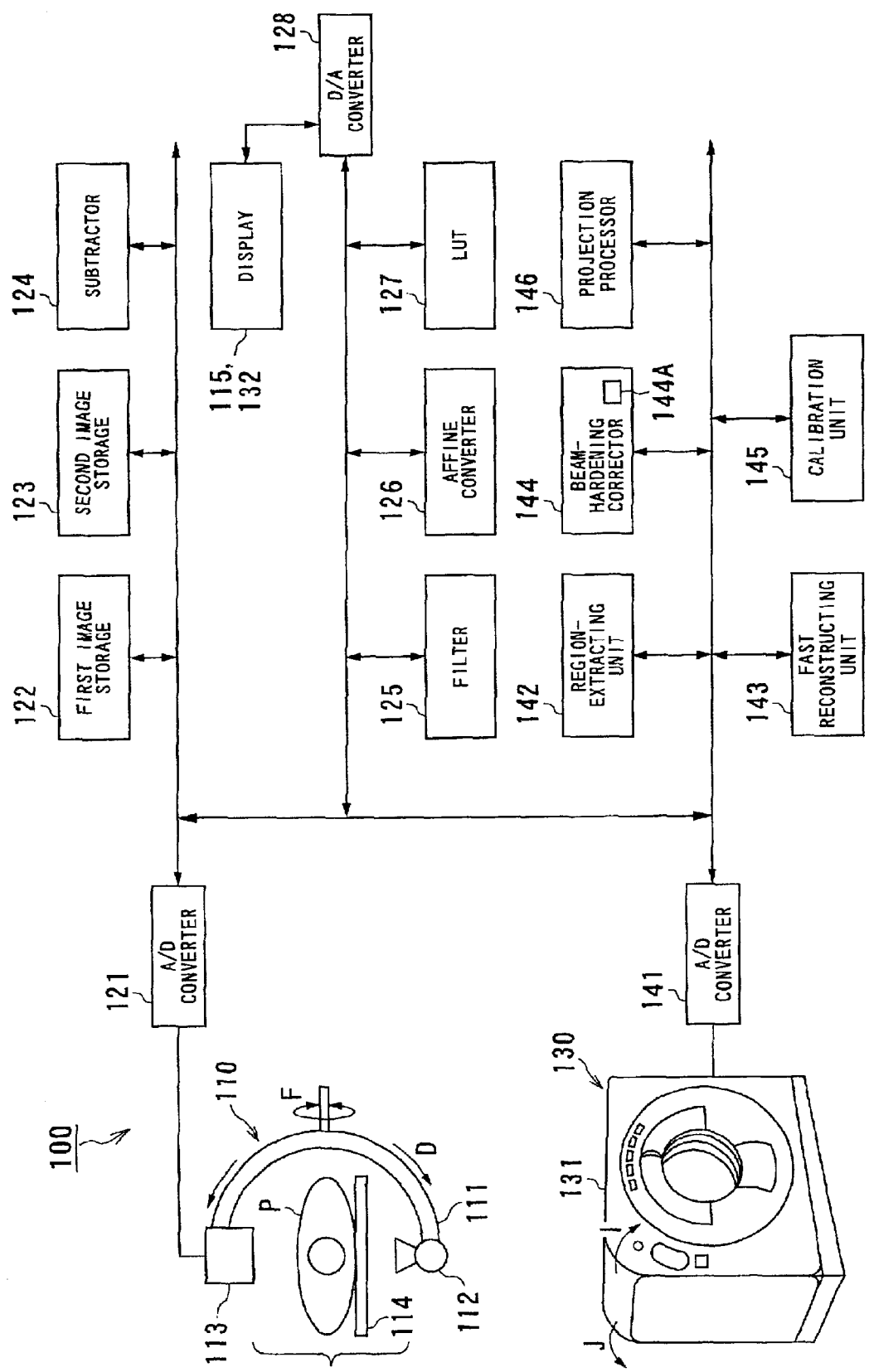
FIG. 8 shows a functional block diagram of the IVR-CT system.

As shown in FIG. 8, the control system of the IVR-CT system 100 includes an A/D converter 121, first image storage 122, second image storage 123, subtractor 124, filter 125, affine converter 126, LUT127, D/A converter 128, and display units 115 and 132, which are identical in construction to those explained in the foregoing first embodiment. The control system further includes the CT gantry 131 having therein a mechanism for causing both the X-ray generating unit and the X-ray detector to rotate at a fast speed. The control system further includes, as a control system of the CT scanner 130, an A/D converter 141, fast reconstructing unit 143 dedicated to fast reconstruction, beam hardening corrector 144, calibration unit 145 that is in charge of various types of correction, such as focus correction to coop with the expansion of a target of the X-ray tube, 3D image processing units including region-extracting unit 142, projection processor 146, X-ray control unit (not shown), and controller (not shown) to manage the operations of those various components.

The region-extracting unit 142 corresponds to the extracting unit of the present invention, the projection processor 146 corresponds to the projection unit of the present invention, the fast reconstructing unit 143 corresponds to the reconstructing unit of the present invention, and the beam hardening corrector 144 corresponds to the correcting unit of the present invention.

Figure 10A:
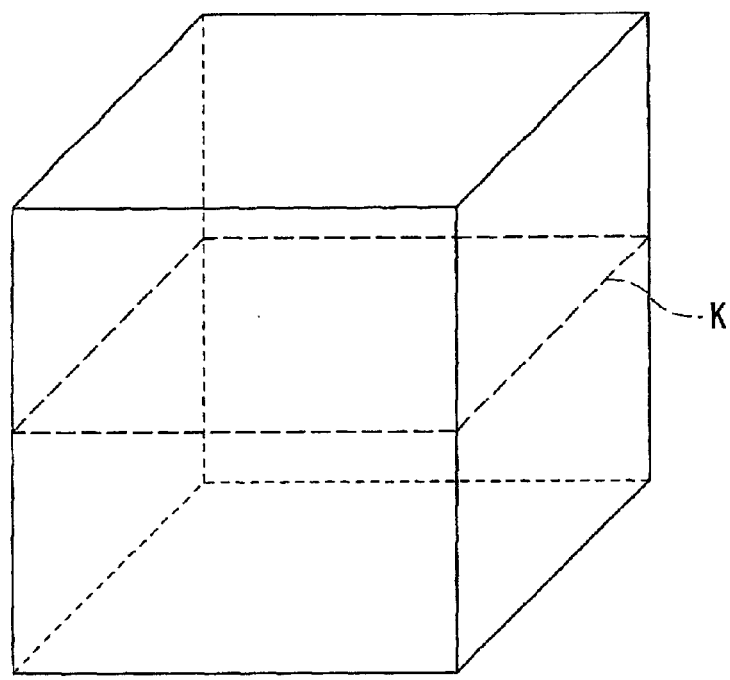
FIGS. 10A and 10B illustrate 3D data handled by the IVR-CT system.
Figure 10B:
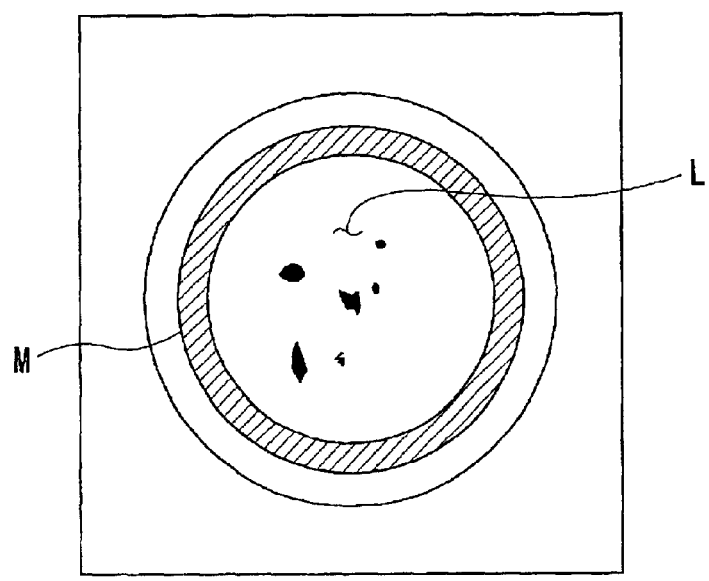

The region-extracting unit 142 is configured to apply threshold processing to a set of 3D reconstructed data in order to extract regions containing a contrast agent (that is, blood vessels L shown in FIG. 10B). For instance, when a CT value at a region of the contrast agent (i.e., blood vessel) is Ac and a CT value at a region of a bone is Ab, the relationship of Ac>Ab is generally true, provided that the contrast agent is directly injected into a region to be examined or therearound. Thus, for example, a value of (Ac−Ab)/2 is assigned to the threshold to extract the contrast agent region (i.e., the blood vessels L in the example of FIG. 10B). Alternatively, the threshold may be a value selected simply from values ranging from Ac to Ab, not limited to the value of (Ac−Ab)/2. Still alternatively, it is possible to previously set a certain values of the threshold as a default value. In this case, it is also preferred that the default value is changed manually via a not-shown input device.

Figure 11:
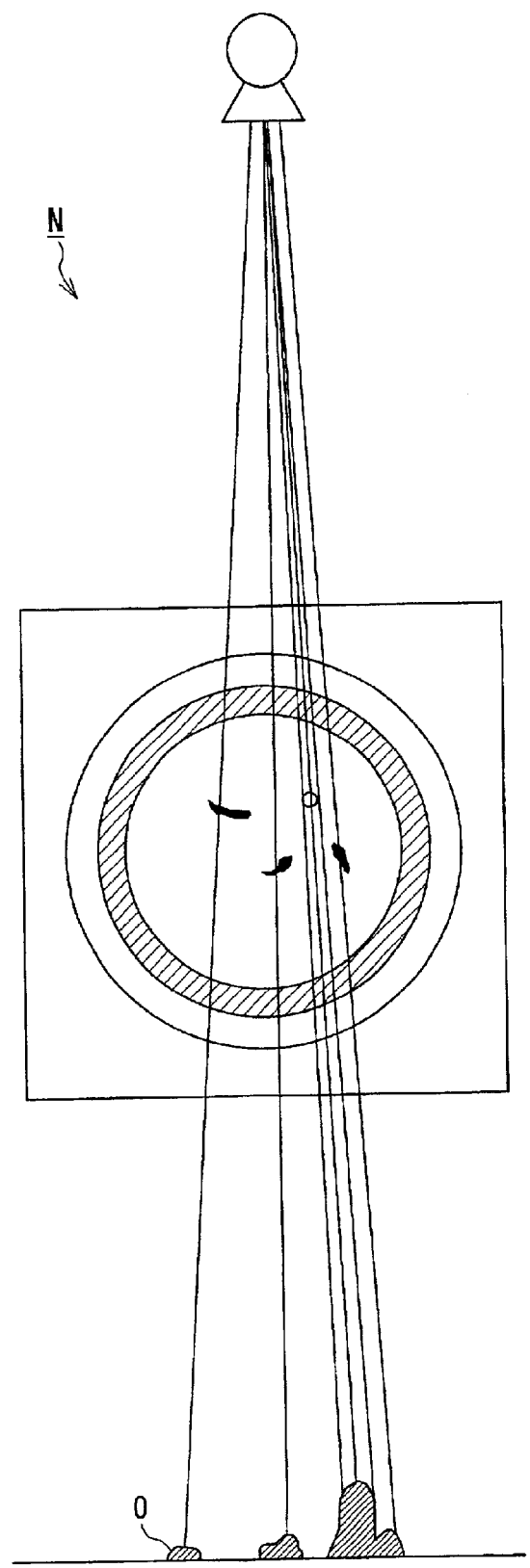
FIG. 11 shows the principle of re-projection processing carried out by the IVR-CT system.

The projection processor 146 uses, as shown in FIG. 11, an optical system N which is completely the same as that of a CT scanner scanning only the extracted regions, so that the contrast agent regions are projected to obtain projection data of only the contrast agent. This processing is called re-projection processing.

The beam hardening corrector 144 is constructed to correct the projection data that has been re-projected by the projection processor 146. The correction of the beam hardening due to the contrast agent is also conducted using a correction table 144A stored in the corrector 144.

In addition to reconstruction processing on scanned projection data in ordinary conditions, the fast reconstructing unit 143 is configured to carry out, again, reconstruction processing on projection data which has been corrected by the beam hardening corrector 144.

Processing Procedures

Referring to FIGS. 7 to 11, the procedures of processing for reconstruction conducted with beam hardening correction will now be described.

First, an object to be examined is laid on the tabletop 114b of the couch 114, and then X-ray fluoroscopy is carried out by the angiography system 110. As is known, for carrying out this fluoroscopy, not only the positions of the couch 114 and/or the tabletop 114b but also the position and attitude of the C-shaped arm 111 are adjusted to move them as shown by the arrows X and D to G. The X-ray tube 112 is then driven to start the radiation of X-rays, while the X-ray detector 113 detects X-rays that have transmitted the object P. The dose of the X-rays are kept lower, so that the fluoroscopy can be realized. Under the fluoroscopy, a catheter is inserted into the object P to reach the vicinity of a target region to be examined, at which a contrast agent is directly injected through the catheter for the purpose of CT images. The contrast agent may be injected directly into a blood vessel, if necessary, under the fluoroscopy.

Figure 9:
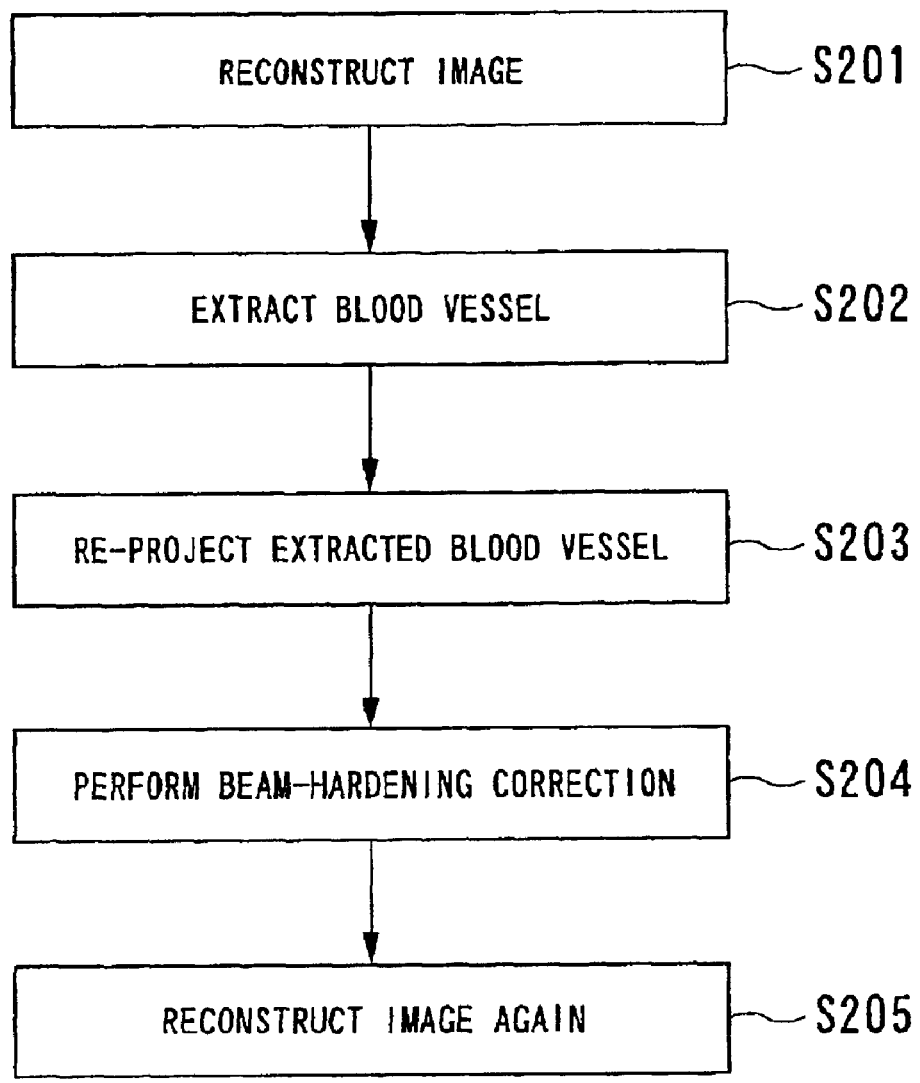
FIG. 9 is a flowchart outlining part of a series of procedures of processing carried out by the IVR-CT system.

Specifically, as shown in FIG. 9, in the fast reconstructing unit 143, acquired projection data P$\theta$(U, V) are subjected to reconstruction processing under ordinary conditions (step S201). Although omitted in this explanation, if the correction of distortions and/or calibrations are desired, like the first embodiment, such correction will be carried out as pre-processing before the reconstruction at step S201.

The reconstruction at step S201 produces a set of 3D data as illustrated in FIG. 10A. The 3D data then undergoes the processing with a threshold, with the result that, as described before, one or more regions in which the injected contrast agent is present are extracted (step S202). Such regions can be pictorially shown in FIG. 10B. The threshold is determined to be a value of (Ac−Ab)/2, wherein Ac is a CT value at a region of the contrast agent and Ab is a CT value at a region of a bone.

Then, using the optical system N which is the same as that for a CT scanner scanning only the regions extracted by the threshold processing, the projection data are projected again (i.e., re-projected) to calculate projection data 0 consisting of data from the contrast agent (step S203).

FIG. 11 pictorially depicts projection data extracting only the regions of the contrast agent (i.e., the regions of blood vessels). The calculated data 0, which is approximately similar in nature to the DSA values explained in the foregoing first embodiment, are subjected to the processing in the beam hardening corrector 144 in order to obtain correcting values P$\theta$c(U, V), like the first embodiment. Because the first embodiment has been explained under the DSA mode, the correction table 144A has been formed to correct the DSA values. However, the present embodiment explains the DA mode, so the correction table 144A is directed to the correction of acquired raw projection values and can be formed by replacing the "DSA values" stored in the correction table 144A according to the first embodiment by "projection values."

In the beam hardening corrector 144, corrected projection data are calculated by adding the obtained correcting values P$\theta$c(U, V) to the already acquired projection data P$\theta$(U, V). That is, the corrected projection data of "P$\theta$(U, V)+P$\theta$c(U, V)" are provided, so that the correction of the beam hardening is completed (step S204). The corrected projection data of "P$\theta$(U, V)+P$\theta$c(U, V)" are then reconstructed again by the fast reconstructing unit 143 (step S205).

As described above, in the IVR-CT system 100, the X-ray CT scanner 130 is able to first reconstruct an CT image from transmission data acquired using the X-ray tube in the CT gantry 131. In the X-ray CT scanner 130, one or more regions of blood vessels (i.e., the regions in which the contrast agent is present) are extracted from the reconstructed image through processing using a certain threshold. The extracted blood vessels are re-projected to produce re-projected data, as shown in FIG. 11, and then the re-projected data are corrected in its beam hardening with the use of the correction table 144A, which has been described in the first embodiment. The corrected re-projected data are again reconstructed. In this way, the reconstruction processing is carried out twice with the correction process toward the beam hardening placed therebetween two times of reconstruction steps. It is therefore possible to remove artifacts on account of a contrast agent injected.

Fifth Embodiment

Figure 12:
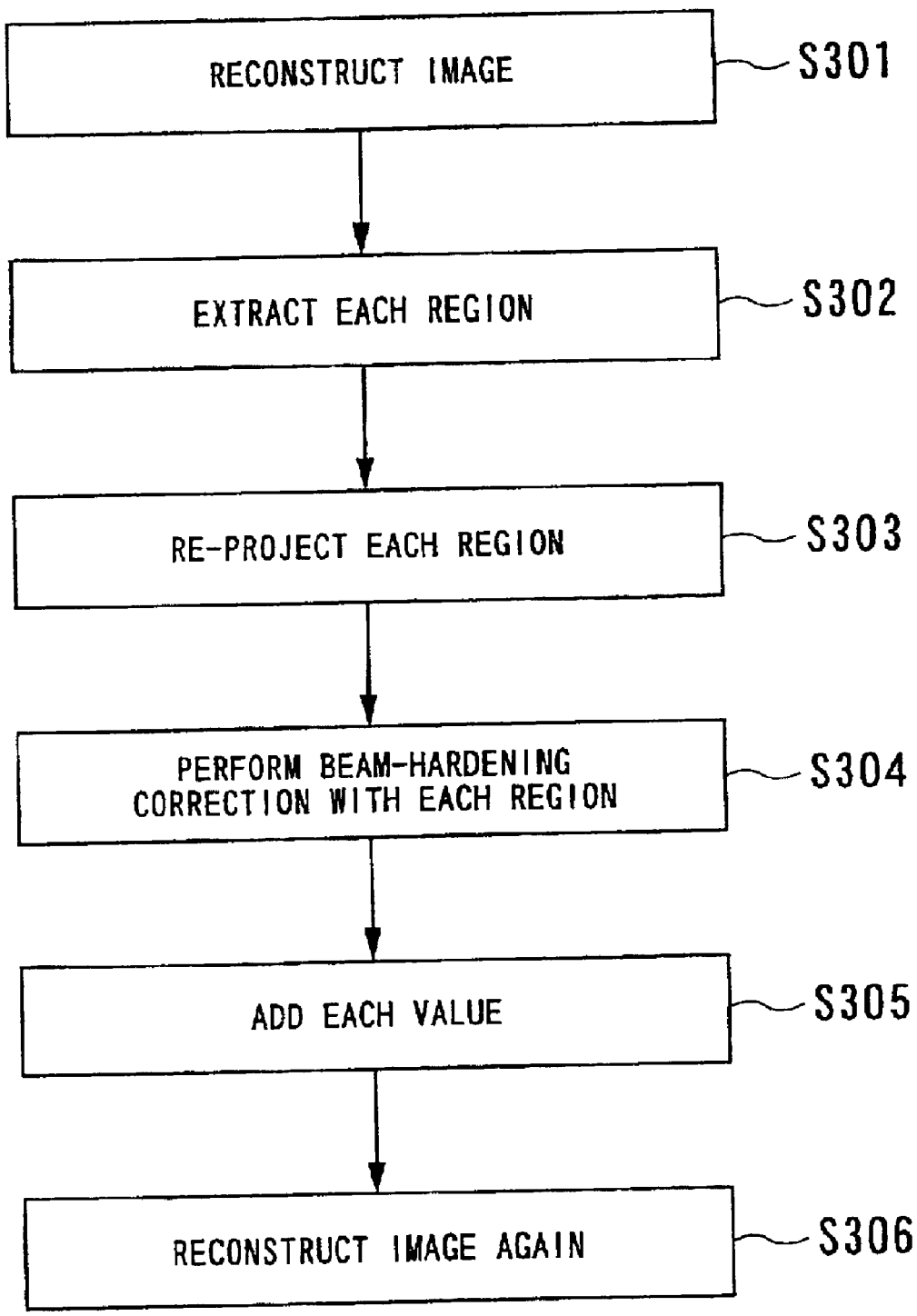
FIG. 12 is a flowchart outlining part of a series of procedures of processing carried out by the IVR-CT system as another embodiment of the present invention.

Referring to FIG. 12, a fifth embodiment of the present invention will now be described. The present fifth embodiment is modified from the fourth embodiment, in which, in addition to the correction toward the beam hardening caused by an injected contrast agent, the beam hardening attributable to elements other than the contrast agent, such as a bone or a soft tissue, can be corrected.

Practically, the processing for such correction is outlined in FIG. 12 carried out by the X-ray CT scanner 130 of the IVR-CT system 100. Like the foregoing fourth embodiment, projection data Pθ(U, V) by the X-ray CT scanner 130 is reconstructed in an ordinary fashion, thus providing a three-dimensional image data (step S301). The produced 3D image data then experiences the processing involving thresholds so that plural images each including only one of a contrast-agent region, a bone region, a soft-tissue region, and a background region (i.e., air region) are produced separately (step S302).

In cases where the density of the contrast agent is higher at least in the body of an object, by reason of, for example, the contact agent is directly injected to the vicinity of a region to be diagnosed, the thresholds can be decided blow. When A1 is a CT value of the contrast-agent region, A2 is a CT value of the bone region, and A3 is a CT value of the soft-tissue region, a relationship of A1 (e.g., approx. 2000 to 3000)>A2 (e.g., approx. 1000 on average)>A3 (e.g., approx. zero on average) is realized. Hence, by way of example, a threshold to distinguish the bone region from the contrast-agent region is set to (A1−A2)/2, while another threshold to distinguish the soft-tissue region from the bone region is set to (A2−A3)/2. This way of setting the thresholds enables each of the regions to be extracted separately. The thresholds may not be restricted to those values, but any amounts are usable if only the regions are separately extracted.

Each of the extracted regions is re-projected so as to produce the projection data of only the contrast-agent region, only the bone region, and only the soft-tissue region, respectively (step S303). There are provided and stored in advance individual correction tables 144A dedicated to correction of the beam hardening due to the contrast agent, the bone, and the soft tissue, respectively. Thus, those correction tables 144A are referred, region by region, to determine correcting values Pθc(U, V) for the contrast agent, Pθb(U, V) for the bone, and Pθs(U, V) for the soft tissue, respectively, and the correction of the beam hardening are carried out (step S304). To be specific, the obtained correcting values are taken into account by adding them to the acquired projection data, so that projection data "Pθ(U, V)+Pθc(U, V)+Pθb(U, V)+Pθs(U, V)" are produced (step S305). The produced projection data "Pθ(U, V)+Pθc(U, V)+Pθb(U, V)+Pθs(U, V)" are then subjected to the reconstruction processing again (step S306).

Accordingly, besides the operations and advantages similar to those in the foregoing fourth embodiment, the beam hardening occurring on account of bones and soft tissues can be corrected together with the correction of that due to the contrast agent. Entire artifacts attributable to such typical constituents as a contrast agent, bones, and soft tissues can be eliminated or largely reduced. Further, the correcting operation can be effective, because all the kinds of correction are done in the same step.

A modification employable by both of the fourth and fifth embodiments is provided. That is, instead of the projection in the "re-projection processing" carried out using the optical system having substantially the same construction as the X-ray CT scanner, another optical system may be used, where parallel beams to each other are presumably radiated. Such optical system results in a shortened period of time for calculation of the re-projection, making the processing faster.

The present invention is not restricted to the configurations and processing explained in the foregoing various embodiments, but a person having ordinary skill in the art is able to create a variety of other modifications within the scope of the present invention.

For example, the mode under which the correction processing is performed can not be limited to the foregoing ones. In the first and fourth embodiments, the 3D-angiography system and IVR-CT system have been configured to perform the correction under the DSA and DA modes, respectively. Those modes are not always fixed. The 3D angiography system and IYR-CT system are able to perform the correction under the DA and DSA modes, respectively. In particular, when it is desired that the 3D-angiography system operates under the DA mode, it can be realized by additionally adding the components in charge of the DA mode shown in FIG. 8, such as the region-extracting unit and the projection processor, to the constructions shown in FIG. 2.

Furthermore, the control system of the IVR-CT system explained in the fourth embodiment can be realized in a different way. In the fourth embodiment, the control system is placed to be used in common for both the angiography system and the X-ray CT scanner. Alternatively, the control system may be arranged separately for each of the angiography system and the X-ray CT scanner, where an interface is added to perform communication of signals between both of the control systems. In this case, the construction concerning the beam-hardening correction may be reduced into practice in either control system or both the control systems.

It is not always true that the correction of the beam hardening due to the contrast agent is automatically activated, like each of the foregoing embodiments. Alternatively, there can be provided two modes of a first mode under which the beam-hardening correction is carried out and a second mode under which the beam-hardening correction is not carried out, and selection means to select either mode in response to, for example, an operator's command. In this configuration, preferably, the selection means is configured such that the selection is made on menus on the display 39 (115, 132). It is also preferable to put a menu to select the mode in the screen image for setting reconstruction conditions. In addition to the selection of performance of the beam-hardening correction toward a contrast agent, the beam-hardening correction toward each of a bone and a soft tissue can be selected. The above selectable configuration is advantageous particularly to the IVR-CT system in shortening a processing time and improving a throughput, because the correction can be selected so that unnecessary processing for the correction is avoided. The correction is normally unnecessary when a contrast agent whose density is relatively lower is injected by way of a vein for CT scanning alone.

Moreover, the IVR-CT system can adopt another type of X-ray CT scanner. For example, the gantry of the X-ray CT scanner can be constructed so that it is moved on rails to and from the angiography system. This rail-type of gantry allows the angiography system to be used independently from the X-ray CT scanner. If necessary, the gantry can be moved to combine into the angiography system, so that the IVR-CT system can be formed. The movement of the gantry also makes it possible that the X-ray CT scanner works solely, from the angiography system. In such a case, it is convenient that the foregoing selection means are provided to selectively halt the beam-hardening correction.

In the foregoing various embodiments, the image processing apparatus according to the present invention has been reduced into practice in the configurations functionally combined with the medical imaging modalities such as the angiography and IVR-CT systems. As other embodiments, the image processing apparatus according to the present invention may be realized as a fluoroscopic X-ray imaging system or a multi-purpose X-ray diagnostic imaging modality. In addition, the medical imaging modality according to the present invention may not be limited to the foregoing IVR-CT system provided with an X-ray imaging system for X-ray examination and the X-ray CT scanner for CT examination. As an alternative, the X-ray imaging system may be configured to perform CT examination solely or other than its original X-ray examination, while the X-ray CT scanner may be configured to perform X-ray examination solely or besides its inherent CT examination.

Although the description above contains many specificities, these should not be construed as limiting the scope of the invention but as merely providing illustrations of some of the presently preferred embodiments of the present invention. Thus the scope of the present invention should be determined by the appended claims.

What is claimed is:

1. An image processing apparatus for processing a plurality of sets of projection data to visualize an internal structure of an object to be imaged, the plurality of sets of projection data being acquired by radiating an X-ray onto the object in a multitude of directions, the apparatus comprising:
    a plurality of correction tables formed corresponding to different X-ray tube voltages and formed to selectively be used in response to a specified X-ray tube voltage, each correction table defining a correcting value corresponding to a change in density of the contrast agent in a region of the object in which the contrast agent is present;
    a correcting unit configured to correct the projection data based on the correcting value obtained from any one of the correction tables so as to avoid influence of beam hardening of the projection data, the beam hardening being caused due to a contrast agent injected into the object; and
    a reconstructing unit configured to reconstruct the corrected projection data into an image of the object.

2. The image processing apparatus of claim 1, wherein each of the correction tables is substituted for a correction table formed corresponding to a representative of the different X-ray tube voltages as long as a change in the voltages is smaller than a given amount.

3. The image processing apparatus of claim 1, further comprising a processing unit configured to calculate a subtraction value, pixel by pixel, between two sets of the projection data acquired in each direction before and after injecting the contrast agent into the object,
    wherein the correcting value defined in each of the correcting tables is a correcting value set to the subtraction value.

4. The image processing apparatus of claim 1, wherein the correcting unit is configured to selectively perform the correction of the projection data depending on a command.

5. The image processing apparatus of claim 1, wherein the plurality of correction tables are set for a plurality of parts of the object, each part being a target for imaging and being categorized depending on which constituent selected from at least a bone and a soft tissue has an influence on the projection data.

6. An image processing method for processing a plurality of sets of projection data to visualize an internal structure of an object to be imaged, the plurality of sets of projection data being acquired by radiating an X-ray onto the object in a multitude of directions viewing the object, the method comprising:
    correcting the projection data based on the basis of a correcting value obtained from any one of a plurality of correction tables so as to avoid influence of beam hardening of the projection data, the beam hardening being caused due to a contrast agent injected into the object, the plurality of correction tables being formed corresponding to different X-ray tube voltages and being formed to selectively be used in response to a specified X-ray tube voltage, and each correction table defining the correcting value corresponding to a change in density of the contrast agent in the region of the object in which the contrast agent is present; and
    reconstructing the corrected projection data into an image of the object.

7. The image processing method of claim 6, further comprising calculating a subtraction value, pixel by pixel, between two sets of the projection data acquired in each direction before and after injecting the contrast agent into the object,
    wherein the correcting value defined in each of the correction tables is a correcting value set to the subtraction value.

8. A medical imaging modality comprising
    a data acquiring unit including a device configured to generate an X-ray and a device configured to detect the X-ray, both devices being supported face to face by a supporter so that projection data composed of X-ray transmittance data mapped at each pixel are acquired in a multitude of directions viewing the object, an object being imaged being placed between the devices; and
    an image processing apparatus configured to process the plurality of sets of projection data to visualize an internal structure of the object, wherein the image processing apparatus comprises:
        a plurality of correction tables formed corresponding to different X-ray tube voltages and formed to selectively be used in response to a specified X-ray tube voltage, each correction table defining a correcting value corresponding to a change in density of the contrast agent in a region of the object in which the contrast agent is present;
        a correcting unit configured to correct the projection data based on the correcting value obtained from any one of the correction tables so as to avoid influence of beam hardening of the projection data, the beam hardening being caused due to a contrast agent injected into the object; and
        a reconstructing unit configured to reconstruct the corrected projection data into an image of the object.

9. The medical imaging modality of claim 8, wherein each of the correction tables is substituted for a correction table formed corresponding to a representative of the different X-ray tube voltages as long as a change in the voltages is smaller than a given amount.

10. The medical imaging modality of claim 8, further comprising a processing unit configured to calculate a subtraction value, pixel by pixel, between two sets of the projection data acquired in each direction before and after injecting the contrast agent into the object, wherein the correcting value defined in each of the correcting tables is a correcting value set to the subtraction value.

11. The medical imaging modality of, claim 8, wherein the plurality of correction tables are set for a plurality of parts of the object, each part being a target for imaging and being categorized depending on which constituent selected from at least a bone and a soft tissue has an influence on the projection data.

* * * * *